US009976962B2

(12) United States Patent
Markovsky et al.

(10) Patent No.: US 9,976,962 B2
(45) Date of Patent: May 22, 2018

(54) ASSAY ANALYSIS

(71) Applicant: Charm Sciences, Inc., Lawrence, MA (US)

(72) Inventors: Robert J. Markovsky, Brentwood, NH (US); Stanley E. Charm, Boston, MA (US); Paul E. Graham, Dracut, MA (US); Richard T. Skiffington, North Reading, MA (US)

(73) Assignee: Charm Sciences, Inc., Lawrence, MA (US)

( * ) Notice: Subject to any disclaimer, the term of this patent is extended or adjusted under 35 U.S.C. 154(b) by 0 days. days.

(21) Appl. No.: 15/835,979

(22) Filed: Dec. 8, 2017

(65) Prior Publication Data

US 2018/0100805 A1    Apr. 12, 2018

Related U.S. Application Data

(63) Continuation of application No. 13/819,064, filed as application No. PCT/US2011/049170 on Aug. 25, 2011.
(Continued)

(51) Int. Cl.
*G01N 21/75*   (2006.01)
*G01N 21/84*   (2006.01)
(Continued)

(52) U.S. Cl.
CPC ............. *G01N 21/75* (2013.01); *G01N 21/78* (2013.01); *G01N 21/8483* (2013.01); *G01N 2201/0627* (2013.01)

(58) Field of Classification Search
CPC .... G01N 2201/00; G01N 21/75; G01N 21/78; G01N 21/77; G01N 33/00; G01N 27/4163; G01N 27/416; G01N 27/26
(Continued)

(56) References Cited

U.S. PATENT DOCUMENTS

| 5,035,862 A | 7/1991 | Dietze et al. ................ 422/68.1 |
| 5,985,675 A | 11/1999 | Charm et al. .............. 250/208.1 |

(Continued)

FOREIGN PATENT DOCUMENTS

| GB | 0312802.2 | 6/2003 | |
| WO | WO 2009/035981 | 3/2009 | ........................ 35/10 |

(Continued)

OTHER PUBLICATIONS

Scil SPOTCHEM EZ Chemistry Analyzer Operation Manual, Veterinary excellence USA Dec. 2009, p. 1-102.
(Continued)

*Primary Examiner* — Christine T Mui
(74) *Attorney, Agent, or Firm* — MacCord Mason PLLC

(57) ABSTRACT

Apparatus and assemblies for the detection of at least one analyte in a sample are shown and described. In one embodiment, the assembly generates a test result from an assay and includes an integrated reader and incubator, wherein the incubator incubates the assay as the reader generates the test result. The reader typically has an optical detector aligned with a light source for detecting a plurality of transmission of light on the assay. The result is systems and methods to improve the detection of the presence and/or absence of at least one analyte in a sample.

20 Claims, 15 Drawing Sheets

Related U.S. Application Data

(60) Provisional application No. 61/454,771, filed on Mar. 21, 2011, provisional application No. 61/377,287, filed on Aug. 26, 2010.

(51) Int. Cl.
*G01N 21/78* (2006.01)
*G01N 33/00* (2006.01)
*G01N 27/26* (2006.01)

(58) Field of Classification Search
USPC ............... 422/50, 82.01, 82.03; 436/171
See application file for complete search history.

(56) References Cited

U.S. PATENT DOCUMENTS

| | | | |
|---|---|---|---|
| 6,124,585 A | 9/2000 | Riedel et al. | 250/208.1 |
| 6,136,610 A | 10/2000 | Polito et al. | 436/514 |
| 6,319,466 B1 | 11/2001 | Markovsky et al. | 422/56 |
| 6,475,805 B1 | 11/2002 | Charm et al. | 436/514 |
| 6,582,659 B1 | 6/2003 | Murata | 422/64 |
| 7,097,983 B2 | 8/2006 | Markovsky et al. | 435/7.1 |
| 7,312,084 B2 | 12/2007 | Jakubowiez et al. | 436/43 |
| 7,384,785 B2 | 6/2008 | Wong et al. | 435/345 |
| 7,410,808 B1 | 8/2008 | Saul et al. | 436/514 |
| 7,785,899 B2 | 8/2010 | Saul et al. | 436/518 |
| 8,003,049 B2 | 8/2011 | Fujimoto | 422/64 |
| 8,262,991 B2 | 9/2012 | Carlsen et al. | 422/63 |
| 9,470,678 B2 | 10/2016 | Ding et al. | 33/558 |
| 9,488,657 B2 | 11/2016 | Graham et al. | 33/58 |
| 2002/0127623 A1 | 9/2002 | Minshull et al. | 435/7.92 |
| 2003/0207442 A1* | 11/2003 | Markovsky | A23D 9/00 |
| | | | 435/287.2 |
| 2005/0036148 A1 | 2/2005 | Phelan | 356/446 |
| 2005/0052646 A1 | 3/2005 | Wohlstadter et al. | 356/311 |
| 2005/0201898 A1 | 9/2005 | Borich et al. | 422/82.05 |
| 2005/0220668 A1 | 10/2005 | Conville | 422/57 |
| 2006/0066850 A1 | 3/2006 | Kimura | 356/328 |
| 2006/0239859 A1 | 10/2006 | Ohman et al. | 422/100 |
| 2007/0083335 A1 | 4/2007 | Moerman | 702/19 |
| 2009/0098022 A1 | 4/2009 | Tokhtuev et al. | 422/82.05 |
| 2009/0155921 A1 | 6/2009 | Lu et al. | 436/164 |
| 2009/0269760 A1 | 10/2009 | Samadopour | 435/6 |
| 2010/0012490 A1 | 1/2010 | Hsu | 204/400 |
| 2010/0055721 A1 | 3/2010 | Lambert et al. | 435/7.33 |
| 2010/0151460 A1 | 6/2010 | Winther | 435/6 |
| 2011/0275162 A1 | 11/2011 | Xie et al. | 436/164 |
| 2011/0318755 A1 | 12/2011 | Piasio et al. | 435/7.9 |
| 2014/0141527 A1 | 5/2014 | Ding et al. | 436/501 |

FOREIGN PATENT DOCUMENTS

| | | | | |
|---|---|---|---|---|
| WO | WO 2009/038798 | 3/2009 | | 33/53 |
| WO | WO 2012/027583 | 3/2012 | | 21/31 |

OTHER PUBLICATIONS

Reflotron Plus Operator's Manual Roche Last Updated Nov. 2007 p. 1-111.

NEPHROCHECK Test Kit Package Insert, Astute Medical Inc. 2014, p. 1-20.

\* cited by examiner

ASSAY ANALYSIS

This application is a continuation of U.S. application Ser. No. 13/819,064, filed Feb. 26, 2013, and is based on and claims priority to PCT/US2011/49170, filed Aug. 25, 2011; U.S. provisional application No. 61/377,287, filed Aug. 26, 2010 and U.S. provisional application No. 61/454,771, filed Mar. 21, 2011, all of which are incorporated herein by reference in their entireties.

FIELD OF THE TECHNOLOGY

The present disclosure relates generally to analytical testing, and more particularly to improved test strips for the detection of an analyte.

BACKGROUND

Reagent strips and films are often a helpful analytical tool in the fields of clinical chemistry, analytical medicine and food sanitation diagnostics. For example, it is advantageous to determine or to test, through quantitative or qualitative methods, various matrices, including body fluids such as serum and urine, and food, such as meat products, fruit, vegetables, milk, honey and the like. Such matrices can be tested for a variety of analytes including a variety of chemicals, biochemicals and biological molecules such as bacteria, antibiotics, for example, sulfa drugs, tetracyclines, beta-lactam drugs; toxins, such as aflatoxin, zearalonone, ochratoxin, T-2, and vomitoxin, pesticides such as organo-phosphates and carbamates, and active metabolites, either in materials or on the surface of materials or a combination thereof.

Generally, lateral flow assays are membrane-based test devices in which a sample that is suspected of containing the analyte of interest is placed at or near one end of the membrane strip. The sample is carried to the opposite end of the membrane strip by mobile phase that traverses the membrane strip, for example by capillary action. While traversing the membrane strip, the analyte in the test sample, if any, encounters one or more reagents. The reagents can include binders for the analyte. Binders can be mobile and, therefore, flow with the sample, or be immobilized on the test strip as a capture agent. Depending on the test configuration, either the analyte binder, the analyte itself, or some other reagent in the test system will be captured by the immobilized capture agent and, thereby, produce a detectable signal. The signal can be generated by a label provided within the assay. The detectable signal can be measured, such as by an optical reader.

The presence and, in some cases, the concentration, of an analyte on a reagent strip may be determined by measuring the optical reflectance from an area of development on the strip. For example, the area of development on the strip may be an area of color development. Percent reflectance can be used to determine the result.

Testing commonly occurs in a controlled environment, such as a laboratory, but testing in non-laboratory settings is also common. In some applications speed and ease of use is particularly important. For example, in food processing it would be advantageous for tests to be run in non-laboratory settings because processors must wait for results. Further, it would also be advantageous for tests to be run on trucks during transport of the items. For that reason, it would be advantageous to accelerate the speed of testing, reduce the cost of equipment and tests, improve the ruggedness of the apparatus, and enhance the ease of use and simplicity of operation. In addition, it is advantageous to have confidence that test results are valid. Therefore, systems, methods and devices herein also assist in preventing fraudulent use of pre-run, known negative assays in place of true samples or use of assays pre-marked to provide a negative result that does not reflect the true nature of the sample. It is also desirable to increase the ruggedness of the assays, systems and test procedures.

Therefore, Applicants desire systems and methods for analyte detection without the drawbacks presented by traditional lateral flow assay systems and methods.

SUMMARY

This disclosure provides improved test strips for analyte detection. In one embodiment, a lateral flow assay for the detection of an analyte includes a surface reflectance profile that is generally adapted to enable monitoring the test strip prior to the detection of the analyte. The reflectance profile may include a reference area to monitor a pre-flow development and a test result reference area to monitor a pre-test detection. Typically, at least one flow reference area is adapted to monitor a pre-flow development along the assay. Further, at least one test result reference area is typically adapted to monitor a pre-test detection of the analyte on the assay.

In particular examples, the reflectance profile includes a theoretical light reflectance measurement. The theoretical light reflectance measurement may include a no-flow development theoretical value. In some examples, the no-flow development value is a reflectance value of about 85. For instance, a reflectance value of greater than about 85 generates a signal to deactivate the detection of the analyte.

In other examples, the flow reference area includes at least one downstream flow reference line. The downstream flow reference line may include a theoretical reflectance value after the flow reference line receives reagent flow thereon. Further, the flow reference area may include an intermediary flow reference line and a downstream flow reference line. In some examples, the intermediary flow reference line may include a theoretical reflectance value after the flow reference line receives reagent flow thereon. The theoretical light reflectance measurement may include a no-analyte pre-test development theoretical value. The test result reference area may include at least one test line having a theoretical reflectance value. Further, the test result reference area includes at least one control line having a theoretical reflectance value.

In yet additional examples, the test result reference area includes at least one test line having a theoretical reflectance value and at least one control line having a theoretical reflectance value. Typically, a pre-set difference between the at least one test line's theoretical reflectance value and the at least one control line's theoretical reflectance value activates a test result. Further, a pre-set difference between the at least one test line's theoretical reflectance value and the at least one control line's theoretical reflectance value typically triggers an error. For instance, the error may withhold a test result.

In other embodiments, a lateral, capillary-flow elongated test strip may include at least one reagent for the detection of at least one analyte in a sample. The capillary-flow elongated test strip may include a test zone, a control zone and a surface having a reflectance profile. Typically, the test zone includes immobilized thereon a test zone capture agent that is generally adapted for capturing the at least one reagent. Further, the control zone typically includes at least one control zone capture agent having a different binding affinity for the at least one reagent. The surface may have a reflectance profile that is generally adapted to monitor the test strip continuously, for instance until the analyte is detected. Typically, the test strip generates a detectable signal upon detection of the analyte in the sample.

In some examples, the test strip may include a coding system having at least one reference code with a corresponding testing sequence. The testing sequence may include at least one testing parameter, for instance a temperature adjustment parameter, an optical reader test parameter, a reader channel selection, a combination thereof and the like. In particular examples, the reader test parameter includes an associated feature chosen from a standard curve, a does-response curve and a combination thereof.

In certain examples, the coding system includes a color matrices that is generally associated with a corresponding diagnostic test. The coding system may include a code chosen from a bar code, an RFID tag, a combination thereof and the like. In yet other examples, the test strip includes a peel strip to introduce sample onto the sample absorbing material, and wherein the peel strip includes a color peel tab at one end of the peel strip associated with the color matrices of the corresponding diagnostic test. The test strip may include an opposed second end having a reactor detector material. Typically, the test strip is adapted for selecting the detection of a diagnostic test group chosen from an antibiotic analyte, toxic analyte, analyte class and combination thereof. The test strip may be sized and adapted to be enclosed within a test strip cavity. For instance, the test strip may be sized and adapted to be enclosed within a test strip cavity of a removable incubation module.

In some examples, the test zone includes at least one analyte reference line having a theoretical reflectance value. The theoretical reflectance value may be associated with a flow parameter on the test strip. In addition, the test zone may include a first analyte reference line having a first theoretical reflectance value and a second analyte reference line having a second theoretical reflectance value. The control zone may include at least one control line having a theoretical reflectance value. The theoretical reflectance value may be an optical reflectance value. The control zone may include a first control line having a first theoretical reflectance value and a second control line having a second theoretical reflectance value.

In yet an alternative embodiment, a lateral, capillary-flow elongated test strip includes a test zone, control zone, a surface having a reflectance profile and a coding system. Typically, the test zone includes immobilized thereon a test zone capture agent adapted for capturing at least one binder. Further, the control zone typically includes at least one control zone capture agent, for instance at least one control zone capture agent having a different binding affinity for the at least one binder. The coding system includes at least one coding signal to correspond to a testing sequence to characterize the test strip.

In another embodiment, an assay analysis device may include at least one test line and at least one control line, and whereby the theoretical reflectance value is a comparison between a reflectance value at the test line and a reflectance value at the control line. A reflectance value on the assay that is inconsistent with the theoretical reflectance value may indicate an inadequate flow on the assay. The inadequate flow may trigger a detectable signal to generate a no-result response. The reflectance value on the assay that is inconsistent with the theoretical reflectance value may indicate a prior analyte development on the assay. The reflectance values may suggest prior analyte development may trigger a detectable signal to deactivate the assay measurement apparatus. The reflectance value on the assay that is inconsistent with the theoretical reflectance value may indicate a contaminated optical path.

A reference coding may activate a corresponding diagnostic test in the optical detector. A multichannel reader and the reference coding may activate a corresponding channel in the multichannel reader. The apparatus may include an incubator and the reference coding may activate a corresponding incubation temperature. An instruction for generating a test result may correspond to an image detection on the assay. The image detection may be an optical reflectance value. The assay may include at least one test line and at least one control line, and whereby the optical reflectance value is a comparison between a reflectance value at the test line and a reflectance value at the control line. The apparatus may be adapted to perform a continuous image detection of the assay. The assay may be a lateral flow assay. For instance, the assay may be a lateral, capillary-flow, elongated test strip. Further, the apparatus may include a means for a power source.

In yet another embodiment, a lateral flow assay for the detection of an analyte and having a test zone and a control zone, a surface having a reflectance profile includes at least one flow reference and at least one test result reference. The at least one flow reference area may be adapted to enable monitoring of a pre-flow development along the assay. The at least one test result reference area may be adapted to enable monitoring a pre-test detection of the analyte on the assay.

The reflectance profile may include a theoretical light reflectance measurement. The theoretical light reflectance measurement may comprise a no-flow development theoretical value. The no-flow development value may be a reflectance value of about 85. A reflectance value of greater than about 85 may generate a signal to deactivate the detection of the analyte. The flow reference area may include at least one downstream flow reference line. The downstream flow reference line may include a theoretical reflectance value after the flow reference line receives reagent flow thereon. The flow reference area may include both an intermediary flow reference line and a downstream flow reference line. The intermediary flow reference line may include a theoretical reflectance value after the flow reference line receives reagent flow thereon. The theoretical light reflectance measurement may comprise a no-analyte pre-test development theoretical value. The flow reference may also be the control zone.

The test result reference area may include at least one test line having a theoretical reflectance value. The test result reference area may include at least one control line having a theoretical reflectance value. The test result reference area may include at least one test line having a theoretical reflectance value and at least one control line having a theoretical reflectance value. A pre-set difference between the at least one test line's theoretical reflectance value and the at least one control line's theoretical reflectance value may activate a test result. Further, a pre-set difference between the at least one test line's theoretical reflectance value and the at least one control line's theoretical reflectance value may trigger an error. The error may withhold a test result.

In other embodiments, a lateral, capillary-flow elongated test strip includes a test zone, a control zone and a surface having a reflectance profile. The lateral, capillary-flow elongated test strip may have at least one reagent for the detection of at least one analyte in a sample. The test zone may include immobilized thereon a test zone capture agent that is adapted for capturing the at least one reagent. The control zone may include at least one control zone capture agent having a different binding affinity for the at least one reagent. The reflectance profile may be adapted to enable monitoring of the test strip continuously until the detection of the analyte. Typically, the test strip generates a detectable signal for detecting the analyte in the sample. In some examples, inadequate control line development, for instance according to reflectance and/or transmission at the control line, may trigger an error. In these examples, the error may trigger a signal to generate a no-result response.

The test strip may comprise a coding system having at least one reference code with a corresponding testing sequence. The testing sequence may include at least one temperature adjustment parameter. Further, the testing sequence may include an optical reader test parameter. The optical reader test parameter may include a reader channel selection. The reader test parameter may include an associated feature chosen from a standard curve, a does-response curve and a combination thereof. The reader test parameter may include at least one associated positive control point and at least one associated negative control point. The coding system may include a color matrices. The color matrices may include a color chosen from red, blue, green and combination thereof. The color matrices may be associated with a corresponding diagnostic test. The coding system may include a bar code. The coding system may include an RFID tag.

The test strip may include a first end having a sample absorbing material. The test strip may include a peel strip to introduce sample onto the sample absorbing material. The peel strip may include a peel tab at one end of the peel strip to facilitate movement of the peel strip. The sample absorbing material may be adapted to receive about 0.1 to about 1.0 mL of a fluid. The sample absorbing material may comprise a dry cellulosic material. Further, the test strip may include an opposed second end having a reactor detector material. The test strip may include a releasing area having a mobile phase receptor for the at least one analyte. The test strip may be sized and adapted to be enclosed within a test strip cavity. Further, the test strip may be sized and adapted to be enclosed within a test strip cavity of a removable incubation module. Typically, the test strip is adapted for selecting the detection of a diagnostic test group chosen from an antibiotic analyte, toxic analyte, analyte class, a combination thereof and the like.

The test zone may include at least one analyte reference line having a theoretical reflectance value. The theoretical reflectance value may be associated with a flow parameter on the test strip. The test zone surface may include a first analyte reference line having a first theoretical reflectance value and a second analyte reference line having a second theoretical reflectance value. The control zone surface may include at least one control line having a theoretical reflectance value. For instance, the theoretical reflectance value may be an optical reflectance value. The control zone may include a first control line having a first theoretical reflectance value and a second control line having a second theoretical reflectance value. In some examples, the reflectance profile is adapted to enable monitoring of the test strip prior to the detection of the analyte. Further, the test result may be detected within about thirty to about sixty seconds.

In yet another embodiment, a lateral, capillary-flow elongated test strip includes a test zone including immobilized thereon a test zone capture agent adapted for capturing at least one binder, a control zone including at least one control zone capture agent having a different binding affinity for the at least one binder, a surface having a reflectance profile adapted to enable monitoring of the test strip and a coding system having at least one coding signal, for instance a coding to correspond to a testing sequence to characterize the test strip. The reflectance profile may include at least one flow reference area adapted to enable monitoring of a flow development along the assay, and at least one monitor reference area adapted to enable monitoring of detection of the analyte on the assay.

In some examples, the test strip may include a first end having a sample absorbing material. The test strip may include a peel strip to introduce sample onto the sample absorbing material. The peel strip may include a peel tab at one end of the peel strip to facilitate movement of the peel strip. The sample absorbing material may be adapted to receive about 0.1 to about 1.0 mL of a fluid. The sample absorbing material may comprise a dry cellulosic material. The test strip may include an opposed second end having a reactor detector material. The test strip may include a releasing area having a mobile phase receptor for the at least one analyte. The test strip may be sized and adapted to be enclosed within a test strip cavity. Further, the test strip may be sized and adapted to be enclosed within a test strip cavity of a removable incubation module. Typically, the test strip is adapted for selecting the detection of a diagnostic test group chosen from an antibiotic analyte, toxic analyte, analyte class, a combination thereof and the like, either quantitatively, qualitatively or both.

The test zone may include at least one analyte reference line having a theoretical reflectance value. Typically, the theoretical reflectance value is associated with a flow parameter on the test strip. The test zone may include a first analyte reference line having a first theoretical reflectance value and a second analyte reference line having a second theoretical reflectance value. The control zone may include at least one control line having a theoretical reflectance value. The theoretical reflectance value may be an optical reflectance value. A control zone may include a first control line having a first theoretical reflectance value and a second control line having a second theoretical reflectance value. The theoretical light reflectance measurement may comprise a no-flow development theoretical value. The no-flow development value may be a reflectance value of about 85. The reflectance value of greater than about 85 may generate a signal to deactivate the detection of the analyte.

In other examples, the flow reference area may include at least one downstream flow reference line. The downstream flow reference line may include a theoretical reflectance value after the flow reference line receives reagent flow thereon. The flow reference area may include an intermediary flow reference line and a downstream flow reference line. The intermediary flow reference line may include a theoretical reflectance value after the flow reference line receives reagent flow thereon. The theoretical light reflectance measurement may comprise a no-analyte pre-test development theoretical value. The test result reference area may include at least one test line having a theoretical reflectance value. The test result reference area may include at least one control line having a theoretical reflectance value. The test result reference area may include at least one test line having a theoretical reflectance value and at least one control line having a theoretical reflectance value. A pre-set difference between the at least one test line's theoretical reflectance value and the at least one control line's theoretical reflectance value may activate a test result.

Further, a pre-set difference between the at least one test line's theoretical reflectance value and the at least one control line's theoretical reflectance value may trigger an error. Typically, the error withholds a test result, including generating a no-result response.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

Figure 1:
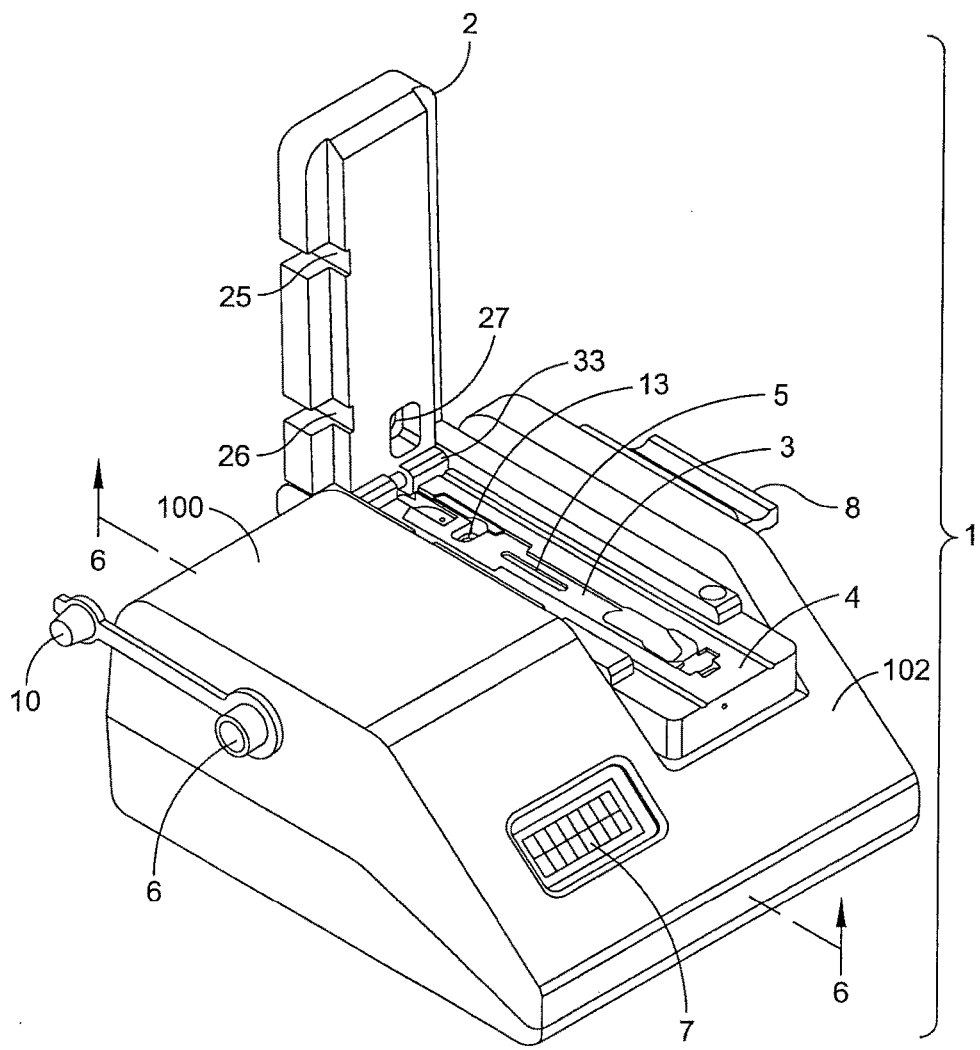
FIG. 1 is a front perspective view of one embodiment of a lateral flow assay system, with an open hood illustrating cavity and base components.

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms. It will be understood that the illustrations are for the purpose of describing embodiments of the disclosure and are not intended to limit the disclosure or any invention thereto.

As introduced in FIG. 1, a lateral flow assay system 1 is shown embodied according to the present disclosure. Lateral flow assay system 1 includes a combined reader 100 and incubator 102. Reader 100 typically includes an imaging detector, such as a sensor, while incubator 102 typically includes an insulated base 4. In some embodiments, the insulated base is a removable assay module 104. Typically, reader 100 first monitors an assay for one, or more, monitoring values, including flow rate, prior analyte development and debris. In various examples, if a proper monitoring value is detected by system 1, incubator 102 incubates the assay and reader 100 generates a test result. However, if an inconsistent monitoring value is detected, system 1 may generate a no-result response.

As shown in FIG. 1, lateral flow assay system 1 is configured to receive an assay and analyze the assay to generate a diagnostic test result. Typically, the assay is a capillary-flow test strip. However, it is within the sprit of this disclosure for any of the assays herein to be other lateral flow assays.

FIG. 1 shows a housing enclosing the reader 100 and incubator 102 as an integral diagnostic unit. Other embodiments include a housing that partially encloses components of lateral flow assay system 1. Typically, the reader includes cavity 3 to receive the assay, and a hood 2 to enclose the assay. The housing may have an exterior and interior, and may be opened, for instance hood 2, to receive an assay into cavity 3. As illustrated in FIG. 1, hood 2 may be lifted and the assay inserted into a heating cavity such as a metallic, for example aluminum, cavity within incubator 102. Typically, cavity 3 is surrounded by insulating material, such as a plastic material, for example a thermoplastic such as polyoxymethylene, known as Deirin (DELRIN is a registered trademark of DuPont) to insulate cavity 3, and does not deform when heated to the temperatures required for generating a test result.

As shown in FIG. 1, hood 2 may be opened into an access position to receive and/or remove an assay within cavity 3 of insulated base 4. Hood 2 may also be configured to substantially seal cavity 3 to enclose the assay in a closed testing position. Openings 25, 26 and 27, in hood 2 allow access to adjustment fasteners 11, 12 and 13 (see FIG. 8), including screws and the like, when hood 2 is in a closed position. In other examples, adjustment fasteners may also be accessed when hood 2 is positioned in an open access position. Typically, adjustment fasteners align cavity 3 in relation to optics, for instance an imaging detector described hereinafter, so that changes on the assay may be detected. For example, test strips may have multiple line developments in various areas on the test strip, as described hereinafter and introduced in FIG. 7. By allowing fine cavity adjustment with the adjustment fasteners through openings 25, 26 and 27, costly and cumbersome system recalibration may be minimized, or avoided. For instance, depending on a particular assay, flow, test and control lines may be in a variety of different position along the assay, as explained below, which may trigger an unexpected reflection, or transmission, value if cavity 3 is not properly adjusted.

As introduced above, cavity 3 may be configured to receive the assay, such as a lateral flow test strip, to position and maintain the assay in an optical alignment with reader 100. In some examples, cavity 3 is shaped with an elongated channel, for instance to receive a lateral, capillary-flow test strip.

Some embodiments of reader 100 are optical analysis readers, which often include a light source and an imaging detector, for example a sensor, that is aligned such that the light from the light source shines onto the assay and is then reflected onto the imaging sensor. An example of optical reader components useful in embodiments herein is described in U.S. Pat. No. 6,124,585 (Apparatus for measuring the reflectance of strips having non-uniform color), issued Sep. 26, 2000, and incorporated herein by reference. Typically, the presence and, in some cases, the concentration, of an analyte on an assay may be determined by measuring, for instance, the optical reflectance from an area of development on the assay. In some examples, percent reflectance may be used to determine the result. In other examples, transmission may be used to detect the result. For instance, the assay may be transparent and include a surface having a transmission profile, similar to the reflectance profile discussed below. This structure and function described in that patent may be adapted by those of ordinary skill in the art in accordance with the disclosure herein to obtain a functioning unit.

Reader 100 may comprise a variety of light sources, including an incandescent bulb, a fluorescent tube, a light emitting diode or the like. In some examples, the light source may be an array of discrete light sources, for instance colored light emitting diodes chosen from red, green, blue and a combination thereof. In yet other examples, the light source may be an individual light source, for instance a singular diode. Typically, the light source is configured and current driven to emit an illumination pattern suitable for reflecting onto the assay, for instance along an elongated test strip. As shown in FIG. 1, light can be directed to the assay, for example through aperture 5 in cavity 3, and then reflected off the assay, back through the cavity aperture 5 and directed to an optical detector.

In one example, an optics circuit board 31 (see FIG. 6) may have a plurality of light emitting diodes (LEDs) mounted thereon, for instance in a predetermined pattern around light-emitting aperture 5. The LEDs may be mounted on one side of optics circuit board 31. An optical detector array may be mounted to the reverse side of the same optics circuit board 31. Further, a first mirror may be positioned below the light-emitting aperture at a pre-determined angle, for instance about three hundred and fifteen degrees, to circuit board 31. A second mirror may be positioned beneath the optical detector, for instance at an angle of about two-hundred and twenty degrees to circuit board 31, such that a substantially 90-degree angle exists between first and second mirrors. A focusing lens may be positioned between the first and second mirrors. Thereby, the light emitted from the LED array may illuminate an assay and then light is reflected therefrom through light-emitting aperture 5, for instance to the first mirror, from the first mirror through the focusing lens to the second mirror, and from the second mirror onto the optical detector. In that respect, the light striking the optical detector may cause the optical detector to generate a measurable voltage. In some examples, the optical detector can output a data stream that can be converted, for example by an on onboard central processing unit, into a series of 128 distinct one-dimensional numeric readings. The 128 readings can be taken multiple separate times and averaged.

In additional examples, a light processor may be coupled to the light source to actuate the light source and provide each light with the appropriate current to generate the desired emission pattern. The light processor may be used to read and store data from the optical detector. The light processor may also be used to adjust the output of an array of discrete light sources such that the emission pattern striking the light detector array has a uniform intensity. The lighting processor may include data storage for the desired light-emission pattern.

Further, the light source may be an LED light source, including a red, green, blue LED device in a single package. For instance, the LED light source for the color sensor can also be three discrete LEDs. Similarly, a single white LED and three discrete photodiodes, with narrow bandwidth responses at the red, green and blue wavelengths, can be used as a detector front-end.

In yet other examples, one LED is used with an optional feedback loop. The feedback loop can use a photodiode to sense light output variation from the single LED. If light output changes, a signal is sent so that an appropriate adjustment can be made, for example, an increase or decrease in current to the LED. Reflectance changes can be the result of the binding of a label, including color particles such as gold beads. Reflectance changes may also be a result of contaminants and interferences in the optical path.

Figure 2:
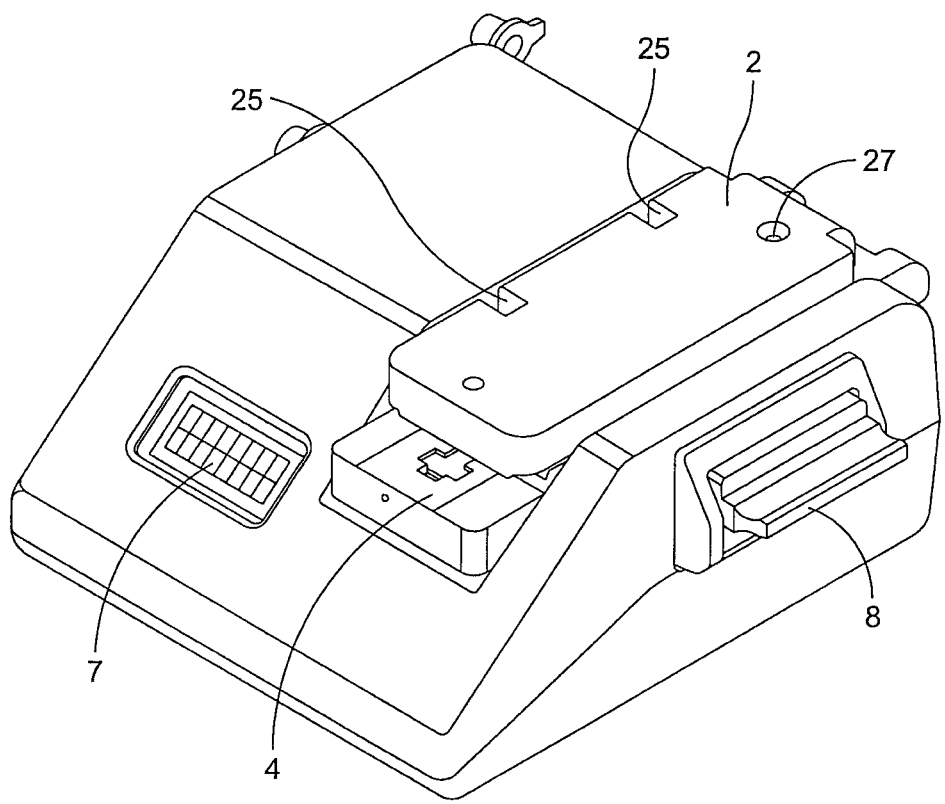
FIG. 2 is a front perspective view of the lateral flow assay system embodiment of FIG. 1, with the hood in a substantially closed position.

As seen in FIG. 2, optical window 8 may be positioned between the assay and reader 100, for instance between a test strip and a sensor. Typically, optical window 8 blocks debris from the assay from contaminating the imaging detector itself, or other system parts used with the sensor, such as lenses and mirrors. In some examples, optical window 8 is clear and includes a handle so that optical window 8 is removable from reader 100 for cleaning. In other examples, the removable optical window may be disposable. In one example, the window material includes clear polyvinyl chloride (PVC) plastic. Window 8 may be mounted on a slide and inserted into reader 100 between cavity 3 and the sensor. The figures show only one removable and cleanable window to block debris, however, other embodiments include additional optical windows covering to protect portions of the optics and/or incubator 102 components.

Regardless of the presence of an optical window, it is possible that dust and debris will infiltrate into reader 100, for example the optical sensor mechanism. To provide an additional cleaning option, air inlet 6 can be provided for compressed air. Air inlet 6 may be covered with a tethered cap 10. In use, clear, optical window 8 is removed, and tethered cap 10 is detached. Compressed air is then blown through reader 100, so that debris collected on, or near, the reader sensor is blown out through the opening previously occupied by window 8.

Some embodiments of reader 100 are programmed with multiple channels, each of which may have separate parameters associated with a related diagnostic test. Each channel selection parameter may include a standard curve, a does-response curve and the like.

Figure 3:
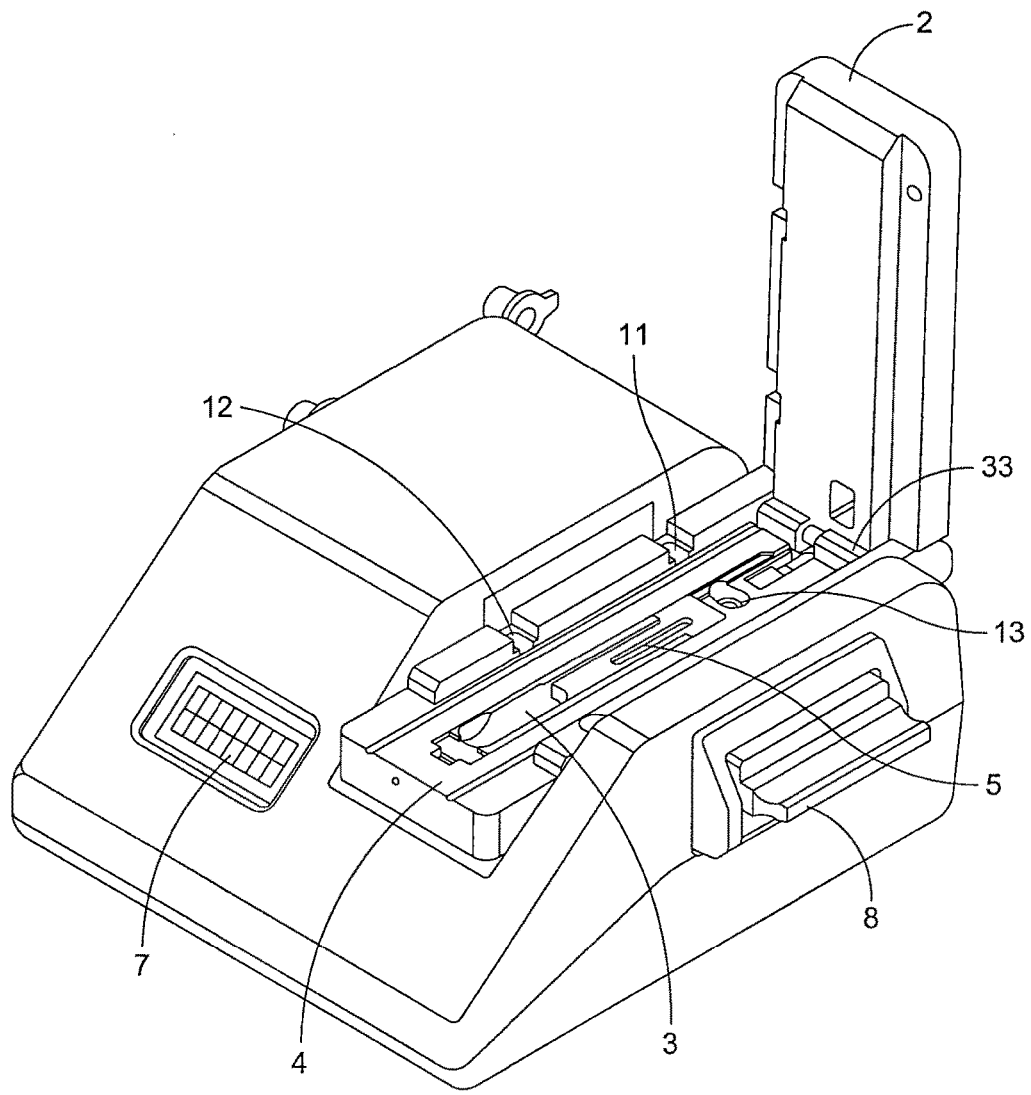
FIG. 3 is a front perspective view of the embodiment of FIG. 1, illustrating examples of cavity and adjustment components.

FIG. 3 shows cavity adjustment fastener 13 in cavity 3, and base adjustment fasteners 11 and 12 in insulated base 4. Openings 25, 26 and 27, in hood 2 allow access to adjustment fasteners 11, 12 and 13, including screws and the like, when hood 2 is in a closed position. In other examples, adjustment fasteners may also be accessed when hood 2 is positioned in an open access position 33. Typically, cavity adjustment fastener 13 aligns cavity 3 in relation to optics, for instance an imaging detector described hereinafter, so that changes on the assay may be detected.

Figure 4:
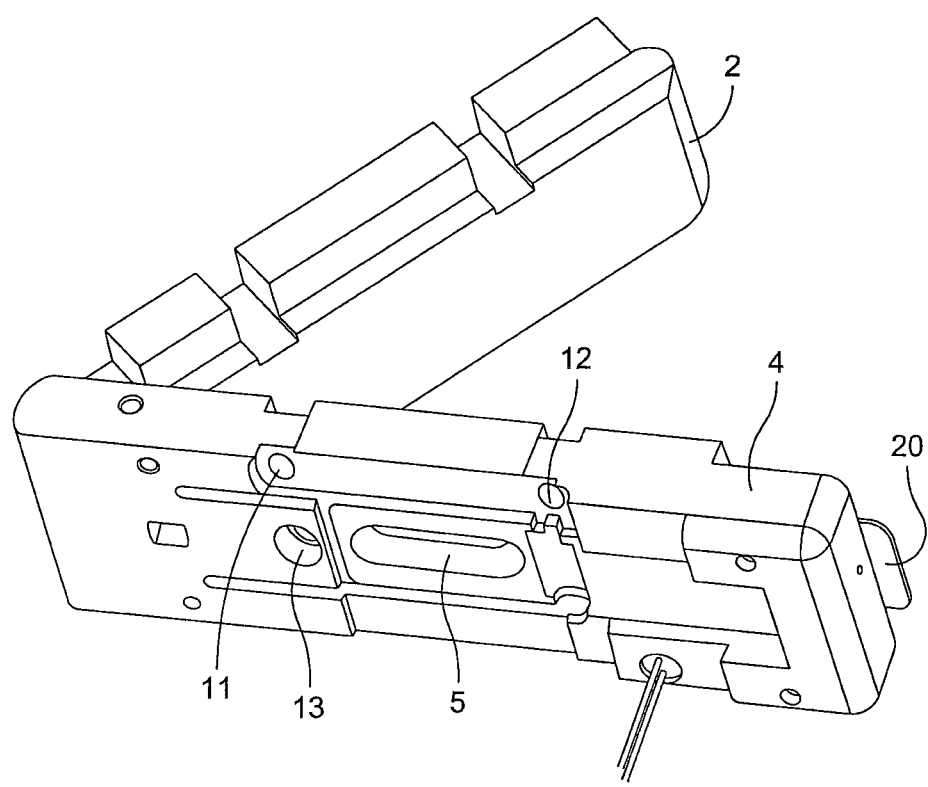
FIG. 4 is an isolated side perspective view of assay base module elements.

FIG. 4 shows one example of insulated base 4 and hood 2 in an opened access position. As shown, the bottom face of base 4 includes openings for cavity adjustment fastener 13, openings for base adjustment fasteners 11 and 12 and light-emitting aperture 5.

Figure 5:
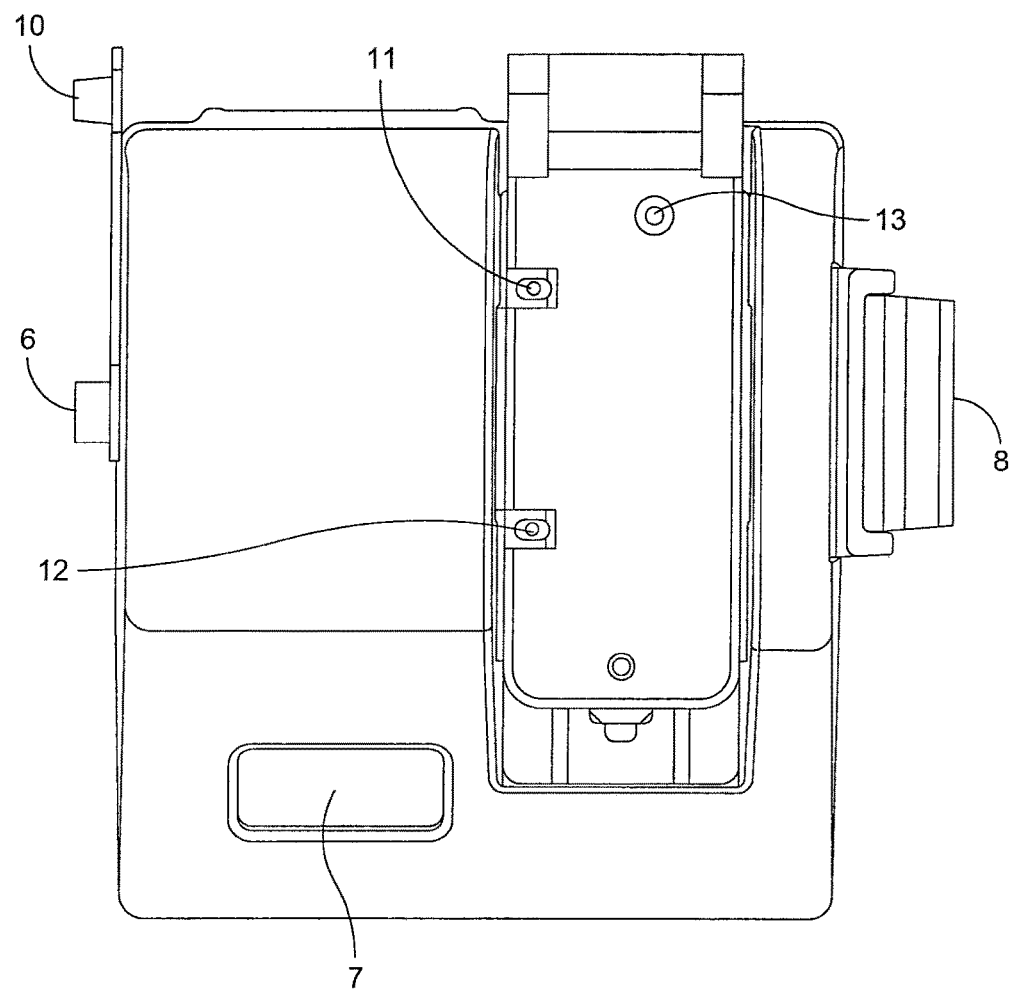
FIG. 5 is a top view of the lateral flow assay system embodiment of FIG. 1 in a closed position.

FIG. 5 shows a top view of lateral flow assay 1 with hood 2 in closed testing position. Window 8 is positioned on the side of the housing to allow the user to remove window 8 for cleaning. As introduced above, air may be inserted through air inlet 6 to further clean debris from optic components.

Figure 6:
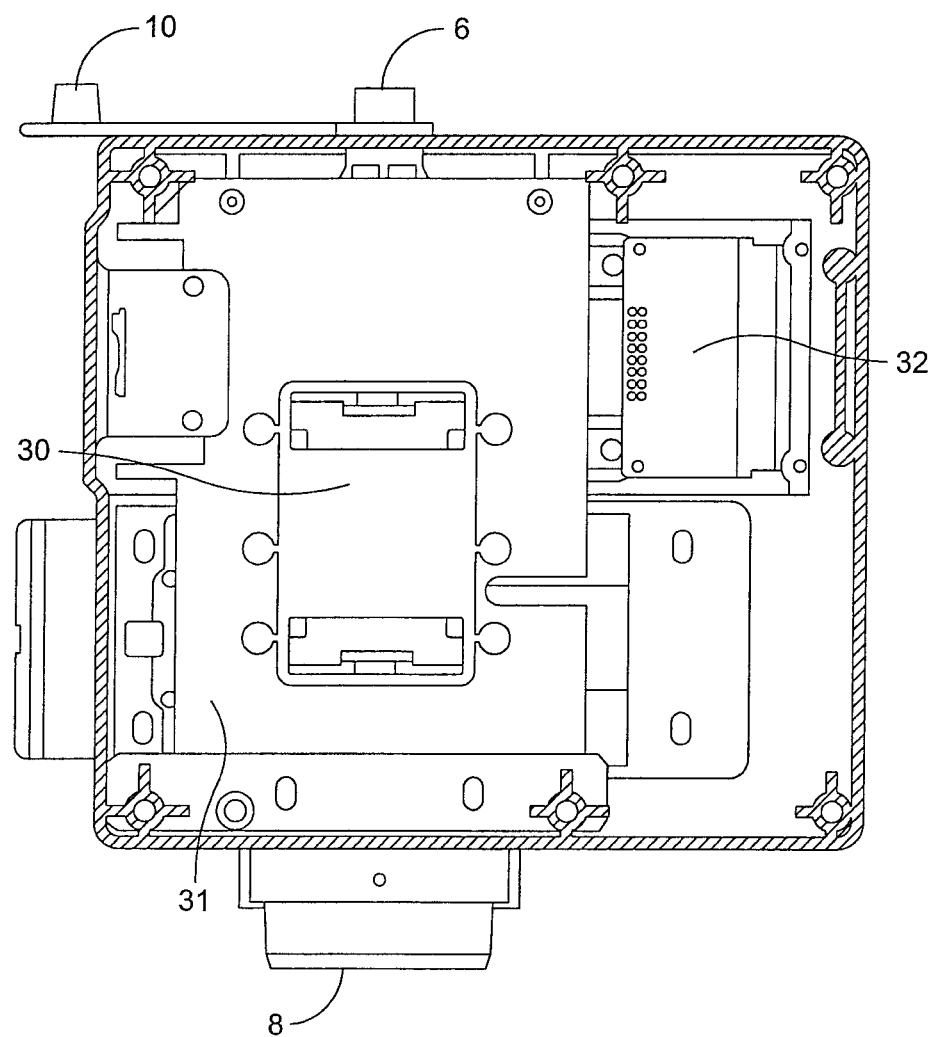
FIG. 6 is a sectional view of the lateral flow assay system embodiment of FIG. 1 taken along lines 6-6, showing circuit board components.

FIG. 6 is a bottom schematic view showing optics board 30, circuit board 31 and display board 32. As shown, LEDs may be mounted on one side of optics circuit board 31. Further, as shown throughout the various figures, lateral flow assay system 1 may include user interface 7. User interface 7 includes an integrated circuit board 31 supporting a display board 32. In one example, user interface 7 allows a user to view flow development. Further, user interface 7 may allow a user to monitor a subsequent flow development after reader 100 has already detected at least one flow development on the assay. Similarly, user interface 7 may display a final test result, including a no-result response.

Figure 7:
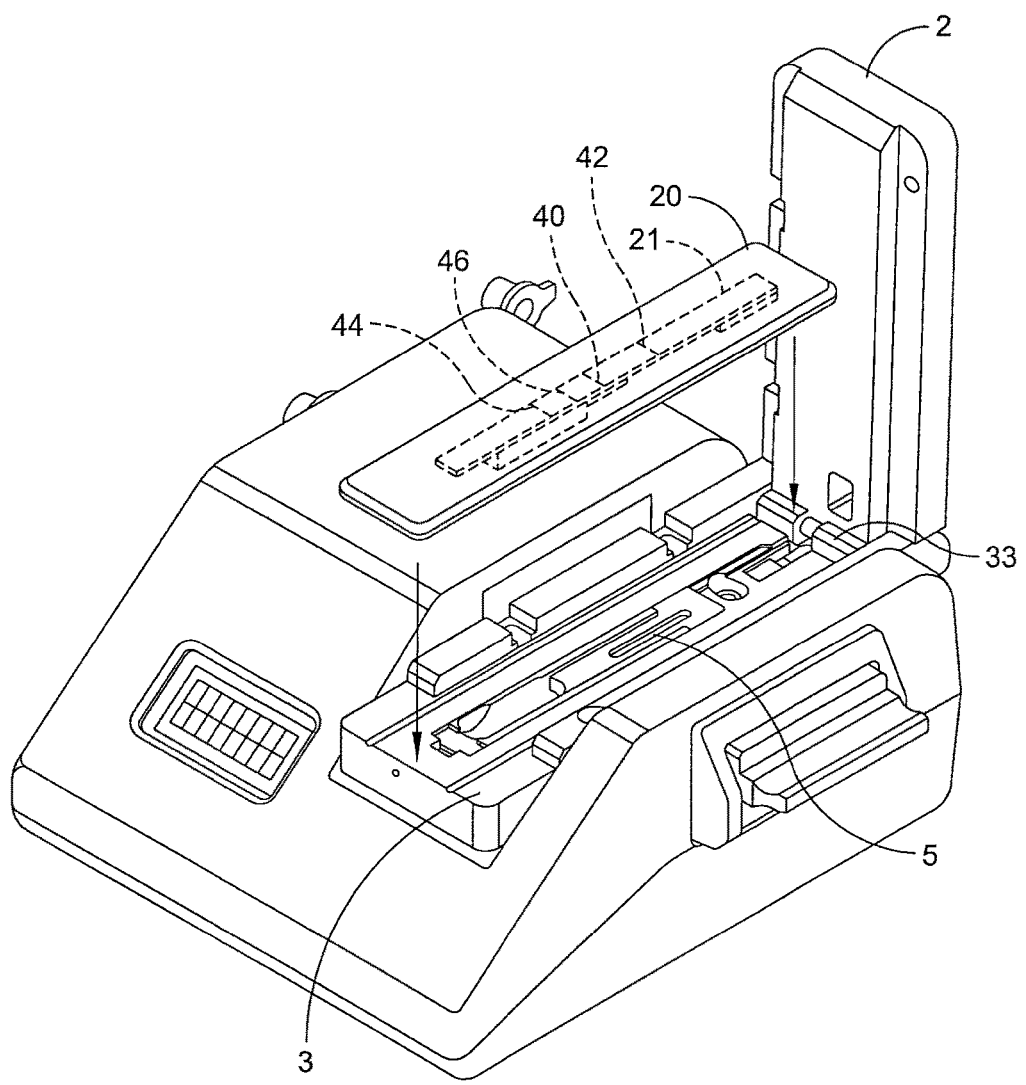
FIG. 7 is a front perspective view of one embodiment of a lateral flow assay system and assay components.

FIG. 7 illustrates one embodiment of hood 2 in open access position with assay 21 secured within test strip enclosure 20, which is adapted to be received by cavity 3. Examples of assay elements for particular diagnostic tests having components useful for embodiments herein include those described in U.S. Pat. No. 7,410,808, issued Aug. 12, 2008; U.S. Pat. No. 7,097,983, issued Aug. 29, 2006; U.S. Pat. No. 6,475,805, issued Nov. 5, 2002; U.S. Pat. No. 6,319,466, issued Nov. 20, 2001; U.S. Pat. No. 5,985,675, issued Nov. 16, 1999 and U.S. patent application Ser. No. 11/883,784, filed Aug. 6, 2007, all of which are hereby incorporated herein by this reference.

Generally, lateral flow assay 21 is membrane-based test device, in which a sample that is suspected of containing the analyte of interest is placed at or near one end of the membrane strip. The sample is carried to the opposite end of the membrane strip by a mobile phase that traverses the membrane strip, for example by capillary action. While traversing the membrane strip, the analyte in the test sample, if any, encounters one or more reagents. The reagents can include binders for the analyte. Binders can be mobile and, therefore, flow with the sample or be immobilized on the test strip as a capture agent. Depending on the test configuration, either the analyte binder, the analyte itself, or some other reagent in the test system, will be captured by the immobilized capture agent and, thereby, produce a detectable signal. The signal can be generated by a label provided within the assay. The detectable signal can be measured, such as by optical reader 100.

Assay 21 may include at least one test line 40 in a test zone and at least one control line 42 in a control zone. A theoretical reflectance value may be a comparison between a reflectance value at test line 40 and a reflectance value at control line 42. A pre-set difference between a theoretical reflectance value at test line 40 and a theoretical reflectance value at control line 42 may activate lateral flow assay system 1, including reader 100, to generate a test result. Further, a separate pre-set difference between a theoretical reflectance value at test line 40 and a theoretical reflectance value at control line 42 may trigger an error. Triggering of the error may cause the microprocessor to withhold a test result, including generating a no-result response, or deactivating reader 100 and/or incubator 102. Other embodiments include a comparison between a transmission value at test line 40 and a reflectance value at control line 42.

A reflectance value on the assay that is inconsistent with the theoretical reflectance value may indicate an inadequate flow in the mobile phase on the assay. For instance, assay 21 may have a flow line 44 with a corresponding theoretical light reflectance measurement. A no-flow development value may be a reflectance value of about 85 on a reflectance scale. Such an inadequate flow may trigger a detectable signal to generate a no-result response. Additional examples include deactivating the lateral flow assay system 1, including deactivating reader 100 and/or incubator 102. In other examples, the flow reference area may include both an intermediate flow reference line 46 with a corresponding theoretical reflectance value and a flow reference line 44.

Similarly, a reflectance value on the assay that is inconsistent with the theoretical reflectance value may also indicate a prior analyte development on the assay. Such a prior analyte development may trigger a detectable signal to generate a no-result response. Further, if the assay is removed prior generating a test result, system 1 may generate a no-response result.

Figure 7A:
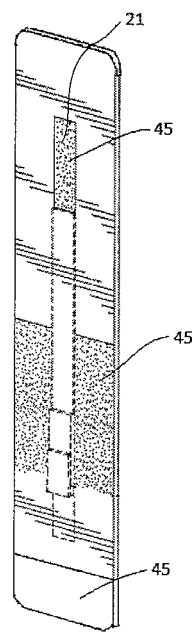
FIGS. 7A and 7B are front perspective and rear views of lateral flow assay embodiments shown in FIG. 7.
Figure 7B:
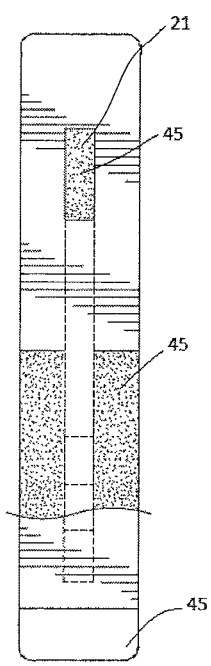

In some embodiments, assays 21 also include a coding reference component(s) 45 with a corresponding testing sequence for lateral flow assay system 1. The coding may be, for example, a color coding, a bar code, an RFID tag or the like, and may be positioned anywhere along the assay so that decoder sensor can decode the reference code, for example on the assay's surface. For instance, in some examples, the coding reference is positioned along the distal end of assay 21 as shown in FIGS. 7A and 7B. Depending on the type of coding on the test strip, reader 100 may require an integrated decoding sensor for example, a bar code reader, an RFID decoder or a color sensor.

Typically, the testing sequence is at least one temperature adjustment parameter within incubator 102 and/or a channel selection of reader 100. Further, the reader test parameter may include an associated feature chosen from a standard curve, a does-response curve and the like. Other embodiments include a variety of testing sequence parameters for the associated diagnostic test being run on the assay.

In some examples, a color matrix, or matrices, reference coding, including a color chosen from red, blue, green and combination thereof, may be associated with a corresponding diagnostic test parameter. When a color coding is used on assay 21, the color can be read by the reader either by a separate optical reading system or the same system that reads the test result. That is, the assay can include a color portion that, after enclosure within the system and test initiation, will be read by the color sensor to determine the reader channel and/or the appropriate incubator temperature. For example, a photodiode with a wide dynamic range of sensitivity to red, green and blue wavelengths can be used as the detector. Red, green and blue LEDs can be used as the light source. Each LED can be turned on sequentially and the detector used to determine the reflectance of each of the colors. A black surface (totally absorbent as containing no color) will produce no reflectance of the given LEDs wavelength and, therefore, the detector will produce low output readings. A white surface will produce maximum reflectance of all three LEDs. Various colors (depending on its content in the surface measured) will produce output from the detector at varying levels.

Such color sensor components may be configured as a separate sensing component within reader 1, or depending on the sensor used to read the test strip result, a singular component that detects both development on the test strip and color coding. In various examples, assays may be coded with a color that defines the test being run. For example, a red color can indicate a test strip to be used to detect beta-lactam antibiotics. Various matrices can also be delineated by the color system. In the red example, after system 1 detects the red color on the test strip, reader 100 and/or incubator 102 may be automatically configured for that specific assay 21, for example by temperature adjustment of incubator 100 and selection of appropriate reflectance test parameters within reader 102. Therefore, in some embodiments, system 1 may an integral diagnostic test unit that is triggered by specific reference codings on the assay.

In other examples, the coding reference may comprise a radio frequency identification (RFID) tag. Such radio frequency signal transmits a signal from the tag to a decoding RFID sensor module. This signal can be used to start the analytic testing sequence, event, channel, temperature or the like in the reader and/or incubator. Similarly, the reference coding may be a bar code, wherein the bar code is placed on the assay and a bar code reader decodes the reference coding and the associated testing sequence information.

Figure 8:
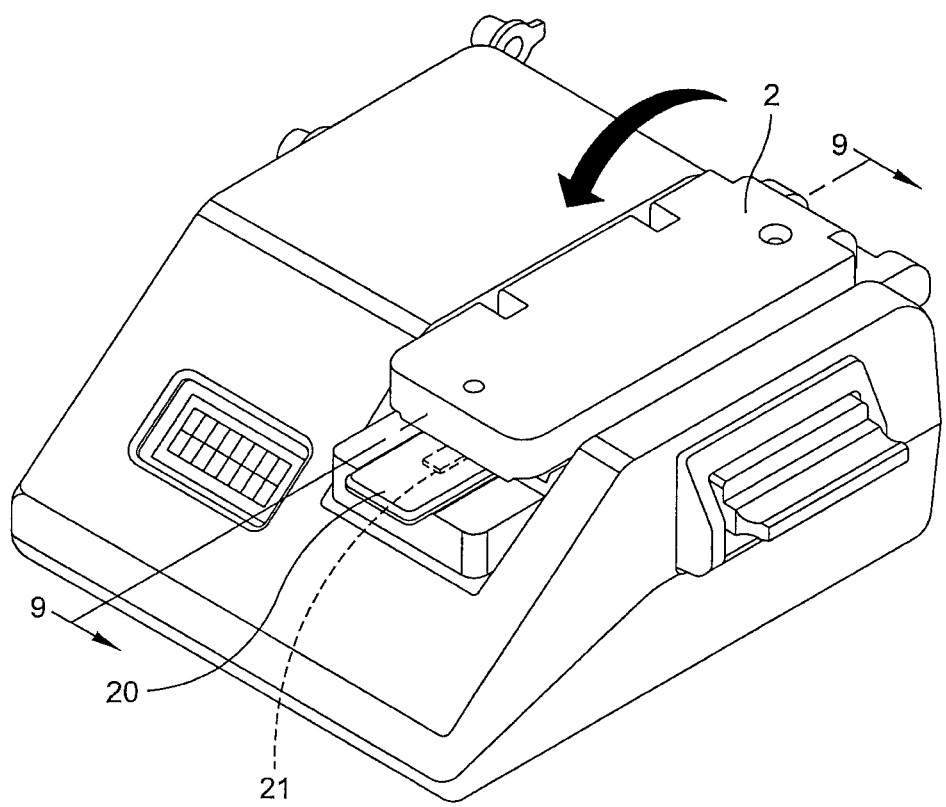
FIG. 8 is a front perspective view of the embodiment of FIG. 7 in a closed position.

FIG. 8 shows assay 21 and assay enclosure 20 positioned within the reader, with hood 2 in a closed position. As shown, hood 2 is pivoted down in a closed testing position, wherein a sensor in the reader is in an optical alignment with assay 21 to generate a test result or a no-result response.

In the closed testing position, incubator 102 may incubate assay 21 in an incubation environment. For instance, incubator 102 may heat and/or cool assay 21 to provide the proper incubation environment for a corresponding assay and diagnostic test. Typically, incubator 102 is in communication to the cavity 3 and is capable of maintaining a consistent temperature within cavity 3 either by heating or cooling at a pre-defined rate. In some examples, incubator 102 includes insulated base 4. In other examples, incubator 102 incubates removable assay module 104, as described hereinafter. The incubator may be a temperature adjustable incubator. In these examples, the temperature adjustable incubator may include a temperature control. In additional embodiments, the temperature adjustable incubator may allow for localized temperature changes.

Incubator 102 may include a heater. The heater may be a ceramic heater, a resister heater element and the like. Typically, cavity 3 is designed to be small so that the heater need only draw minimum current. In that way, heating only essential areas and providing insulation around those areas minimizes power requirements. Use of various heating algorithms can be useful. For example, a proportional integrated derivative (PID) can be used. In other examples, incubator 102 may compensate for localized temperature variations from the selected target temperature, for instance a target temperature according a corresponding testing sequence. Incubator 102 may also compensate for localized temperature variations with an analog, proportional control circuit. In other examples, incubator 102 may also compensate for localized temperature variations with a digital control circuit, for instance by utilizing a PID algorithm or a PID controller. Further, those of ordinary skill would recognize that PI, PD, P or I controllers, and/or algorithms, do not preclude any of the inventions herein. For instance, temperature adjustable incubator may include a digitally controlled potentiometer to allow the microprocessor selection of temperature. In other examples, algorithms are particularly useful when test results are affected by small temperature variations. Embodiments include incubator control systems that eliminate the need for manual adjustment by use of embedded, digital temperature sensors and digital potentiometer that provides both accurate temperature reporting and a mechanism by which a micro-controller can adjust a stand-alone, analog, incubator control circuit.

In additional embodiments, cooling might be advantageous to reduce the incubation environment temperature, for example to stabilize the environment of a test medium and/or sample prior to incubation.

Figure 9:
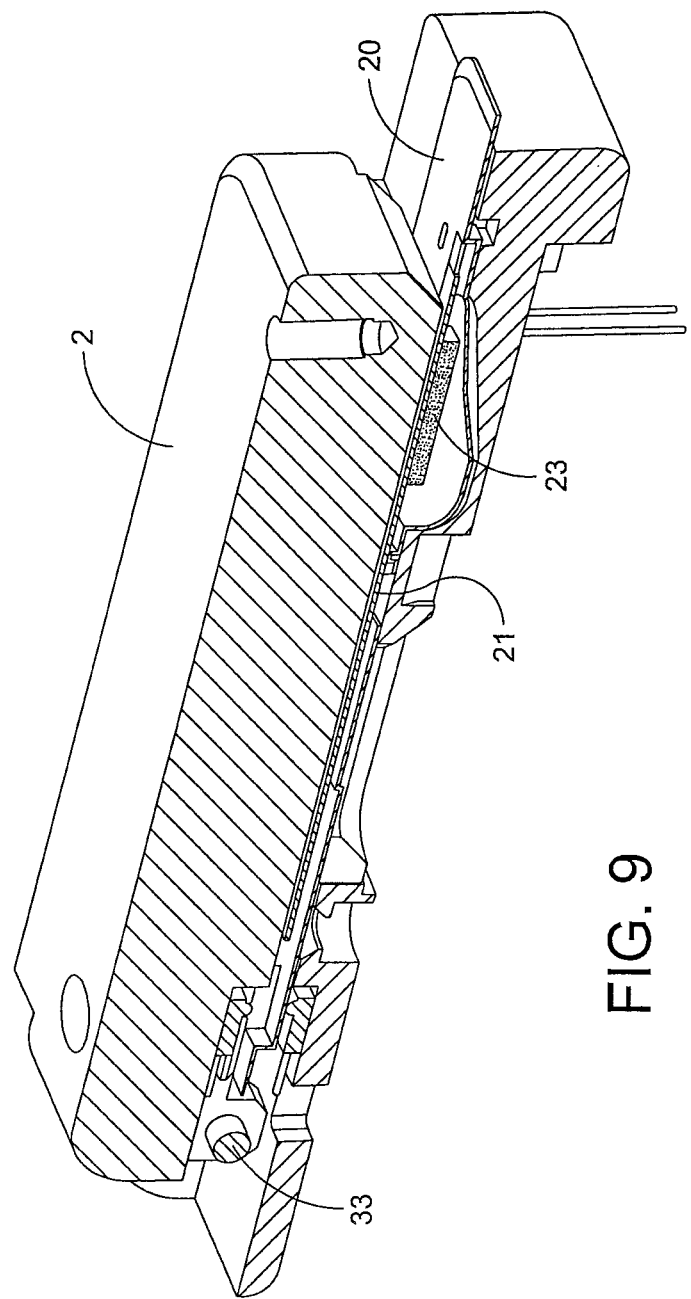
FIG. 9 is a partial cross-section of one example of the embodiment introduced in FIG. 7 taken along 9-9.
Figure 10:
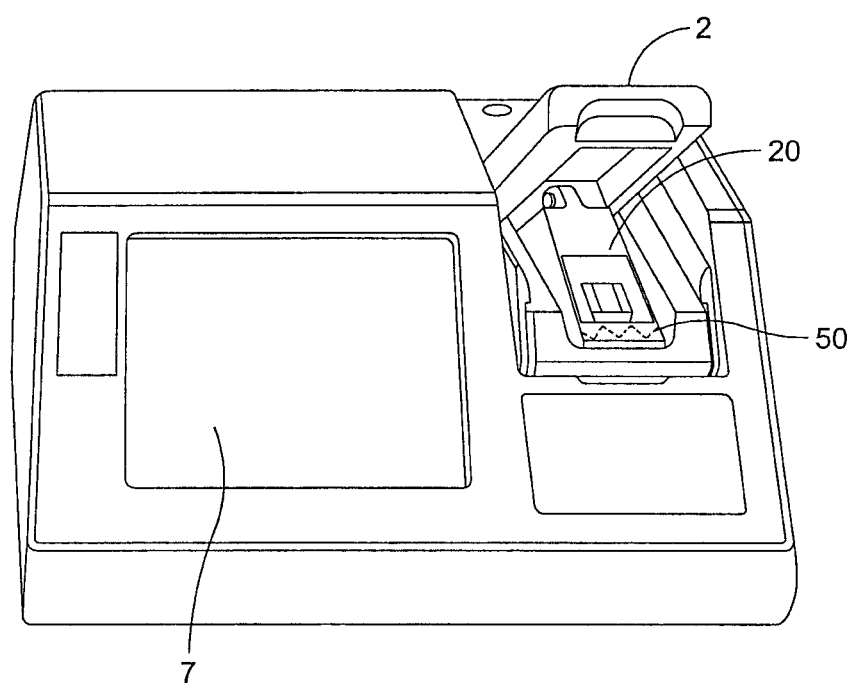
FIG. 10 is a front perspective view of one embodiment of a lateral flow assay system and assay components.
Figure 11:
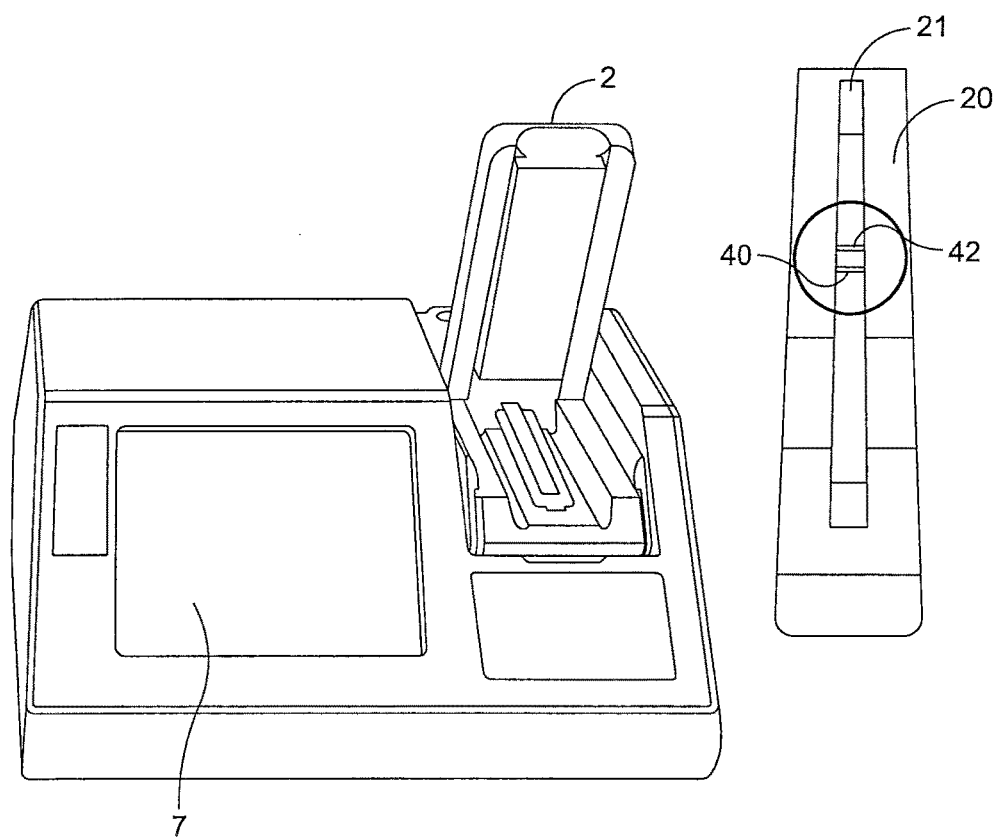
FIG. 11 is a front perspective view of one embodiment of a lateral flow assay system and assay components.

As shown in FIG. 9, test strip 21 may include a first end having a sample absorbing material 23. Further, as introduced in FIG. 10, test strip 21 may have a peel strip 50 to introduce sample onto sample absorbing material 23. Peel strip 50 may include a peel tab at one end of peel strip 50 to facilitate movement of the peel strip 50. Sample absorbing material 23 may be sized and configured to receive about 0.1 to about 1.0 mL of a fluid. Further, sample absorbing material 23 may be composed a dry cellulosic material. Other embodiments include other materials of sample absorbing material 23.

Figure 14:
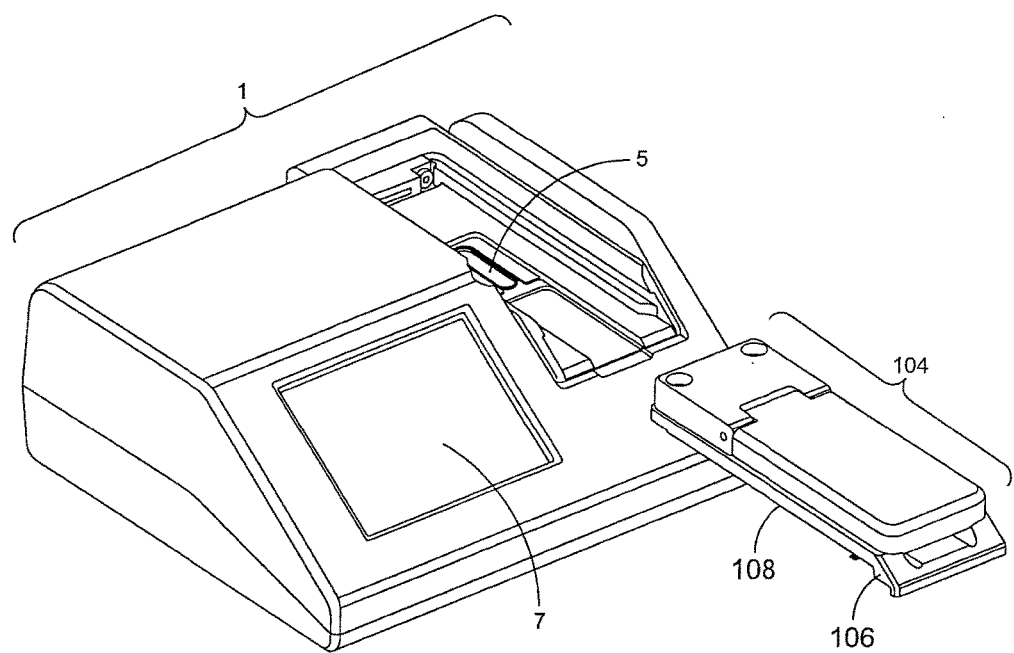
FIG. 14 is a front perspective view of one embodiment of a lateral flow assay system having a removable assay module.

Typically, assay 21 also includes an opposed second end having a reactor detector material. Assay 21 may support a releasing area having a mobile phase receptor for the at least one analyte. Further, assay 21 may be sized and adapted to be enclosed within test strip cavity 3. Similarly, assay 21 is typically sized and adapted to be enclosed, for example enclosed tightly, within an assay cavity 3 of a removable incubation module 104, as seen in FIG. 14. Typically, assay 21 is adapted for selecting the detection of a diagnostic test group chosen from an antibiotic analyte, toxic analyte, analyte class, a combination thereof and the like.

Reader 100 may include a sensor to monitor a test progress, for example on a lateral flow assay, and/or determine a test result from the lateral flow assay. The sensor is positioned relative to assay 21, so that a change on assay 21 can be detected by the sensor. Typically, the sensor is activated when the lateral flow assay is both positioned within cavity 3 and exposed to the consistent temperature within cavity 3 from incubator 102. For example, the sensor can be activated by closing hood 2 that encloses cavity 3. The sensor may include an optical detector and a microprocessor. Typically, the optical detector is aligned in an optical path with the assay and is adapted to acquire an image detection on the assay and is performing a continuous image detection acquisition of the assay.

The sensor may be a single photodiode, multiple photodiodes, a linear photodiode array, a charged couple device, a complementary metal oxide semiconductor and a combination thereof. Therefore, at the same time as incubation and flow, or before, or after incubation and flow is complete, the optical sensors can monitor the assay and compare optical readings, such as reflectance and/or transmission readings, to determine various aspects including sample flow, interference with the optical path such as by debris in the optical path, line development and test result. When the assay and line development falls within preset parameters, the test can continue to completion and provide a final result. Checking of the assay by the optical sensor prior to test completion can provide the user with additional confidence that the test was processed properly.

Typically, the output may be a voltage, current or a digital output proportional to light intensity as determined by signal conditioning circuitry. Some examples of reader 100 include the TSL12T and TSL13T sensors available from TAOS (Texas Advanced Optolectronic Solutions). The TSL12T and TSL13T sensors are cost-optimized, highly integrated light-to-voltage optical sensors, each combining a photodiode and a transimpedance amplifier (feedback resistor=80 M$\Omega$ and 20 M$\Omega$ respectively) on a single monolithic integrated circuit. The photodiode active area is 0.5 mm×0.5 mm and the sensors respond to light in the range of 320 nm to 1050 nm. Output voltage is linear with light intensity (irradiance) incident on the sensor over a wide dynamic range.

In some examples, the microprocessor may be in communication with the optical detector, and in particular with the sensor. In other examples, the optical detector outputs to other logic means. Further, the microprocessor may be adapted to signal the optical detector to perform continuous image detection of the assay to generate the diagnostic test result. The microprocessor may include, or have associated, memory to store information corresponding to an imaging parameter. The memory may include instructions for monitoring a pre-test analysis on the assay and for generating a diagnostic test result on the assay.

In some embodiments having assays with coding references, as discussed herein, the optical detector may have a decoding ability to decode a reference code on the assay. Thereby, the decoding sensor may thereby active a corresponding diagnostic test in reader 100. For instance, the decoding sensor may activate a corresponding channel in a multichannel reader 100 and/or activate a corresponding incubation temperature profile within incubator 102.

The decoding sensor may be a color sensor. For example, the color sensor may be a photodiode with sensitivity to wavelengths chosen from red, blue, green and a combination thereof. In such an example, a color reading an arrangement of photodiodes, each with a specific color filter, is used as the decoding sensor and a white LED (which provides a wide spectrum of light through the 3 bandwidths (Red, Green and Blue)) is used as the light source. When the LED is turned on, the output from each of the photodiodes is obtained to determine the reflectance of that specific color. The decoding sensor may also be an RFID reader or a bar code reader.

Although reference is often made herein to optical reflectance, and optical reflectance readers, a variety of readers may be usefully employed including, for example, transmittance reader, fluorometers, luminometers, bar code readers, radiation detectors (such as scintillation counters), UV detectors, infrared detectors, electrochemical detectors or optical readers, such as spectrophotometers, charged coupled device (CCD) or complimentary metal oxide semiconductor (CMOS) can be used as an image sensor. An optical reflectance reader can be programmed to analyze the test strip through two-dimensional readings, rather than through the one dimensional, 1×128, readings. For example, a 5×128 or 512×492 matrix of "pixels." Such a 2-dimensional reading widens the reflectance capture area to capture reflectance directly from the sides of the test strip.

In other examples, a transmittance reader, such as an ultraviolet Visible Near-Infra red (UV-Vis-NIR) spectroscopy may provide a characterization of the absorption, transmission, and/or reflectivity of the assay. For instance, such an analytical technique may measure the amount of light absorbed on the assay at a given wavelength. Those of ordinary skill in the art would appreciate that a molecule, or part of a molecule, can be excited by absorption. Typically, organic chromophores which absorb strongly in the UV or visible portions of the spectrum nearly always involve multiple bonds, such as C=C, C=O or C=N. This molecular excitation energy may be dissipated as heat, for instance kinetic energy, by the collision of the excited molecule with another molecule, e.g., a solvent molecule, as the molecule returns to the ground state. In other embodiments, the excitation energy may be dissipated by the emission of light via fluorescence. Regardless of the process, an excited molecule may possess any one of a set of discrete amounts of energy, for instance as described by the laws of quantum mechanics. In examples herein, the major energy levels may be determined primarily by the possible spatial distributions of the electrons, and to a lesser extent by vibrational energy levels, which arise from the various modes of vibration of the molecule.

Therefore, in particular examples herein, absorbance measurements may be determined by the concentration of a solute on the assay. For instance, the progress of such a chemical reaction may be followed using a spectrophotometer in reader 100 to measure the concentration of either a reactant or a product over time. In other examples, a transmission spectroscopy may be used for solid, liquid, and gas sampling. Typically, light is passed through the assay and compared to light that has not. The resulting spectrum may depends on the path length or sample thickness, the absorption coefficient of the sample, the reflectivity of the sample, the angle of incidence, the polarization of the incident radiation, and, for particulate matter, on particle size and orientation.

Figure 12:
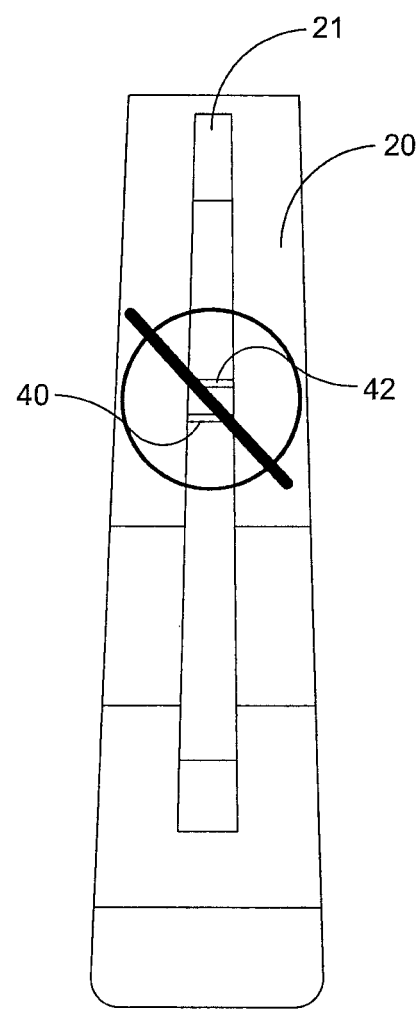
FIG. 12 is an isolated view of the assay illustrated in FIG. 11, showing one example of a prior analyte development before testing triggering an error.

In some embodiments, the sensor monitors assay 21 for prior analyte development before generating a test result. As shown in FIG. 12, prior analyte development on test line 40 and control line 42 indicates an error. A reflectance value on assay 21 that is inconsistent with the theoretical reflectance value may indicate a prior analyte development on assay 21, including a pre-run assay, contaminated assay or the like. The prior analyte development may trigger a detectable signal to generate a no-result, for instance a no-run, response and/or deactivate assay system 1. Other outputs may be indicative of the detected condition and are also within the scope of these inventions.

Further, the sensor may monitor flow development along assay 21 to assess whether an inadequate sample volume has been applied to assay 21, or that excess volume has been applied. For instance, prior to determining the test result, the sensor may monitor the flow progress on assay 21 along flow line 44. In other examples, the sensor will monitor flow progress at both flow line 44 and along the assay, for instance at intermediary flow line 46. The sensor may be configured to sense whether an adequate flow of a reagent occurred on assay 21, while assay 21 was within cavity 3, and/or whether one or more lines, i.e. reflectance or transmission values, were present on assay 21 prior to contact of assay 21 with the sample to be tested.

In addition, the sensor may be configured to detect whether dirt/debris is contaminating the optical path. For instance, the sensor may monitor the optical path for interference such as by debris. To determine that a test has run properly, or that the assay is free of dirt/debris, predetermined optical measurements, such as reflectance values or transmission values, may be stored electronically. The preset values, or preset parameters, can include a theoretical reflectance, or transmission, value from an unused assay (prior to receiving reagents). Preset values may also include values may be one or more theoretical test lines and/or one more theoretical control lines on the assay, and may also include a difference between the theoretical reflectance values for the one or more control lines and the theoretical value for the one or more test lines.

Figure 13:
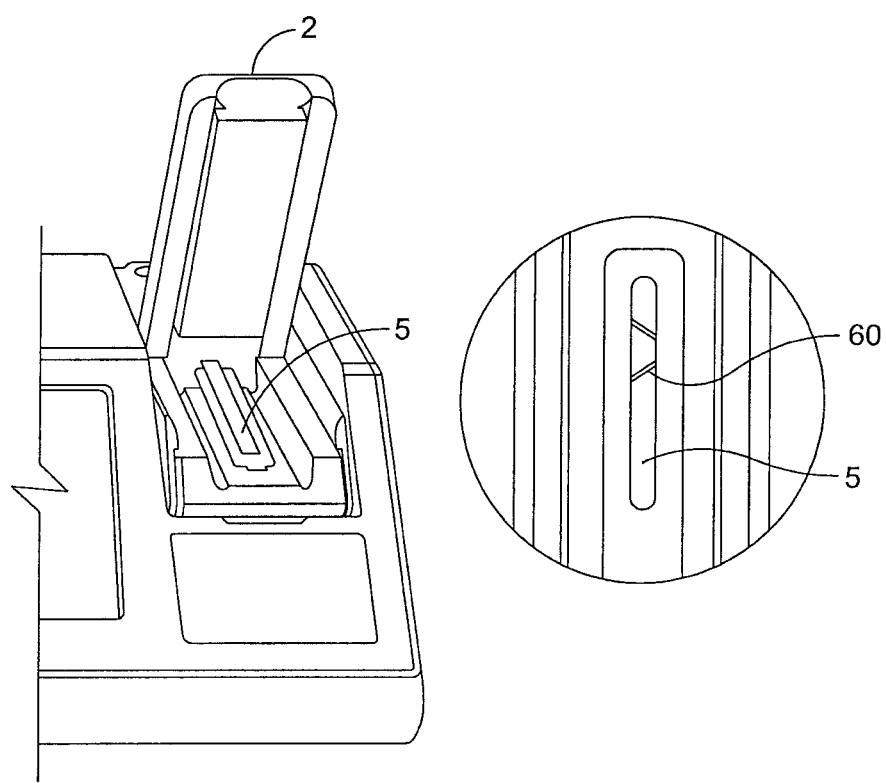
FIG. 13 is a front perspective view of one embodiment of a lateral flow assay system with debris on the imaging detector.

FIG. 13 shows one embodiment of lateral assay system 1, with debris 60 over light aperture 5. In use, a reflectance value on an assay that is inconsistent with the theoretical reflectance value may indicate a contaminated optical path, such as debris 60 as shown here. Lateral assay system 1 may be adapted to generate a no-run response and/or deactivate reader 100 and/or incubator 102 when the sensor detects such an aberration.

In other examples, the optical detector may monitor at least one pre-test parameter after the optical detector has already acquired at least one image detection on the assay. Similarly, optical detector generates a test result from assay 21, for instance by a comparison between at least two lines on the assay, for examples lines 40 and 42 of the test strip depicted in FIG. 7. As indicated above and in the incorporated references, optical detector may compare changes in reflectance values of two lines on the assay, for instance at least one test line 40 and at least one control line 42.

Particular embodiments include configuring the lateral flow assay system to allow concurrent incubation and reading of assay 21. The combination allows sensors to be used to detect not only test results, but also to check parameters that might indicate whether or not flow has occurred on the assay and that such flow caused a proper test result. That is, while sample, including the potential analyte, or analytes, of interest, is flowing on assay 21 and binding is occurring in a mobile phase and on assay 21, the assay is being incubated. By combining reader 100 and incubator 102 into such an integral diagnostic unit 1, results can be achieved quicker than when assays, such as test strips or other test medium, are incubated in one device and then moved to a separate device for reading. For instance, speed-to-result can be enhanced, for example to as little as less than about 60 seconds or even less than about 30 seconds. Generally, such a combined system can be dynamic, sensing changes in the assay as they occur by looking for areas of decreased reflectance and/or transmission anywhere on the unused or not-fully developed assay.

A level of protection is provided to prevent pre-run assays from being read (for example, reader 100 will determine if line development, for instance at flow line 44, intermediary flow line 44, test line 40 and/or control line 42 occurred prior to the time when sample flow could have reached such line) and to prevent incorrect readings caused by debris, or similar interference with system optics.

Various triggers may initiate assay analysis of system 1. For example, closing of hood 2 may initiate test operation, including optical measurement. Alternatively a separate switch can be used to initiate test operation after hood 2 is closed. In either case, a first reading may determine whether a proper assay is correctly position in the system. If assay 21 is detected, a reading sequence is initiated. For example, optical measurement, such as to detect light reflected off assay 21, can utilize values, such as average reflectance values, in certain areas of assay 21. Initially system 1 may analyze the assay to determine if the optical path is clear of interference, such as from debris. Debris can be in any number of locations in the optical path including on assay 21 or assay container 22. Concurrently with analyzing the optical path for debris, or subsequent thereto, the system can analyze the assay to determine if line development has already occurred. That is, whether a proper assay has been inserted into cavity 3. For example, test strips configured to develop within certain areas, such as a test line and control line, should have no development in those areas before the analyte and mobile phase have had adequate time to reach them.

In some examples, lines configured to develop a change in reflectance, and/or transmission, when contacted by reagents and sample should not develop until flow of sample and reagents has arrived and binding has occurred. That flow will not have arrived at the time of an initial, for example about three second, read. As such, if line development is detected at the initial assay analysis, then an error message will be delivered to the user and further readings, for example further optical measurements, can be aborted. In this way, this mechanism can detect the use of pre-run (known negative) assay or pre-marked assays. Generally, when reflectance is reduced on an unused assay, either by the presence of line development or other darkening of the assay away from baseline, the reduction in reflectance can inform the user that something has occurred either on the assay or in the optical path, so that the result should not be accepted.

After initial optical readings are found satisfactory and appropriate reader parameters and incubator temperatures are selected, either manually or automatically, further optical readings, for example approximately fifteen seconds after sample has been applied, can be used to determine whether adequate flow has occurred. For example, optical readings can determine whether or not reagents have flowed between a sample application region and a downstream line such as a test line.

The presence of label, such as colored particles, for example gold sol beads, flowing in the mobile phase, and the resulting reflectance changes on the assay between the sample application area and a first test line, can inform the user that flow is occurring and return an error message if no flow is detected. An assay lacking predictable reflectance changes might either have had no sample flow, or inadequate sample flow. Certain measurements can also indicate whether excessive flow has occurred, as in the case where too great a volume of sample has been applied to a test strip and possible reflectance change due to reagents is overwhelmed by the excessive sample volume. Reflectance changes between the sample application area and result detection areas, such as test line and control line, can be temporary and disappear as the mobile phase flows. If optical measurements are taken such temporary/non-permanent changes can be detected.

If an assay, including a test strip or other assay type, has passed the preliminary readings, system 1 may initiate readings to generate a test result. For example, after approximately thirty seconds test line and control line analysis can begin. When there is enough differentiation, for example percent reflectance difference, between the test and control, a result can be provided. Typically, negative results and more extreme results can be provided sooner and results closer to threshold levels will take longer. For example, in the case of a test in which the reflectance value on the test line relates inversely to the amount of analyte, if the test line reflectance is reduced to a certain level then a negative result can be called. In some examples, if hood 2 is opened while reader 100 is reading the assay, a signal may generate a no-result response.

Reader 100 and/or incubator 102 may be powered by a power source. In some examples for on-site analysis, for instance in rugged environments, the power source may be a vehicle battery. Further, reader 100 may be in communication with an onboard vehicle system.

As introduced in FIG. 14, lateral flow assay system 1 may include removable assay module 104 to be removed from system 1 and cleaned from debris. Typically, removable assay module 104 includes a similar assay cavity as described above, to align assay 21 with optics of reader 100 while in a closed testing position. In some examples, the assay is a lateral flow test strip and the assay cavity within removable assay module 104 is sized to receive the lateral flow test strip.

As discussed above, removable assay module 104 may include a hood. The hood may enclose the assay in a closed testing position and be opened to clean away debris in an open maintenance position when removable assay module 104 is removed from system 1. In some examples, if the hood of removable assay module 104 is opened while reader 100 is reading the assay, a signal may generate a no-result response. Further, removable assay module 104 may have a bottom face having a window 108 to slide in between reader 100 and the assay in a manner so that at least one light aperture 5 aligns with the assay in a closed testing position. Window 108 may be removable and cleanable as discussed above, and further the bottom face may include holes to receive an adjustment fastener to secure removable assay module 104 into an optical alignment with reader 100. In other examples, bottom face 108 may include engagement lip 106 to position bottom face 108 securely with reader 100.

FIG. 15 illustrates a flowchart of one testing sequence embodiment of the present disclosure. As shown in FIG. 15, the diagnostic test may begin with creating an assay. For instance, creating the assay may include adding a test sample to a test medium, such as a lateral flow test strip, e.g. including any of the test strip embodiments previously shown or described. Typically, the test medium is configured to provide a detectable test result after incubation with the test sample. Next, the assay is positioned to an optical sensor, e.g. including any of the sensor embodiments previously shown or described. The assay then undergoes diagnostic testing concurrently with incubation as described herein for the detection of an analyte.

In some examples as shown in FIG. 15, a clear positive or clear negative test result, i.e. a clear positive or clear negative detection of an analyte will end the testing sequence. However, a borderline result will trigger a further development in the testing sequence. Typically, the further development includes continued performance of a diagnostic test with concurrent incubation. In exemplary embodiments having a borderline preliminary result, further development is performed until a clear positive or clear negative test result, which ends the testing sequence.

FIG. 16 illustrates a flowchart of another testing sequence embodiment of the present disclosure. As shown in FIG. 16, the diagnostic test sequence is similar to the sequence introduced in FIG. 15; however, the reader is programmed to perform only a one minute diagnostic test read. Again, a clear positive or clear negative detection of an analyte will end the testing sequence, but a borderline result will trigger a further development in the testing sequence. In some examples, the second or additional diagnostic testing, e.g. any of the testing previously described herein, may also be one minute diagnostic reads. However, those of ordinary skill in the art having this disclosure will recognize other examples include a variety of testing lengths and sequences to meet a particular application or test result.

FIG. 17 shows another testing sequence embodiment of the present disclosure, where the optical sensor decodes an assay reference, e.g. any of the reference embodiments previously shown or described. For instance, the optical sensor may decode the assay reference to initiate a particular diagnostic test, incubation environment or the like.

FIG. 18 illustrates yet another testing sequence of the present disclosure.

In other embodiments, the disclosure includes a lateral flow assay system 1 kit. In this embodiment, the kit may comprise an incubator, e.g. any of the incubators and/or incubator components previously shown or described, and a reader, e.g. any of the readers and/or reader components shown or described.

In yet another embodiment of the disclosure, a method for analyte analysis includes incubating the assay, e.g. including any of the embodiments previously shown or described, and reading the assay to generate a test result, e.g. including any of the embodiments previously shown or described. In particular examples, a diagnostic test method for detecting an analyte in a test sample includes adding a test sample to a test medium, such as a lateral flow test strip, to create an assay, the test medium configured to provide a detectable test result after incubation with the test sample; enclosing the test medium within a hood, the hood configured to enclose a cavity, the cavity configured to receive the test medium and connected with a temperature control source, the temperature control source capable of maintaining a consistent temperature; positioning a sensor, such as an optical sensor capable of reading reflectance from the test medium, relative to the test medium so that a change on the test medium is detectable by the sensor; and activating the sensor, such as by closing the hood, the activation causing the sensor to compare the test medium to a preset parameter. When the test medium is not within the preset parameter, a test result is not provided, and wherein when the test medium is within the preset parameter, the test result is determined from the test medium, the test result indicating whether an analyte was detected in the test sample.

In other embodiments of the methods, a preset parameter can be used to determine either or both whether an adequate flow of reagents occurred on the test strip while the test strip was within the cavity and whether one or more test lines are present on the test strip prior to being contacted by the test sample. To do so the sensor can be configured to continuously analyze changes on the test medium until a test result occurs. The test result can be determined by a comparison between changes, such as reflectance changes, in a first line, for example a test line, and a second line, for example a control line, on the test strip.

A further example of the methods include using preset parameters to compare the test strip, prior to sample flow thereon, including prior to sample application, with the actual strip being used. For example, a blank strip, prior to reagent flow or prior to sample application, will have a theoretical reflectance profile within a predictable range. If areas of reduced reflectance are detected, that did not result from sample/reagent flow on the strip, then it is possible not only that something untoward has occurred with the test strip but also it is possible that the optical path has become contaminated and requires cleaning. Such contamination can be on the strip or within the reader. Generally, an unused test strip should have no areas of reduced reflectance. Any such areas can indicate a problem, whether from dirt/debris, use of a test strip that was already run, or otherwise. In any case, the test result may not be valid.

Numerous characteristics and advantages have been set forth in the foregoing description, together with details of structure and function. Many of the novel features are pointed out in the appended claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

What is claimed is:

1. An apparatus to generate a test result from an assay, said apparatus comprising:
   a. an incubator adapted to incubate said assay in at least one incubation environment; and
   b. a reader having an optical detector aligned with a light source for detecting a first transmission of light on said assay and detecting at least a subsequent transmission of light on said assay that undergoes a change, when present, when contacted with a sample to generate said test result, and wherein said apparatus synchronizes incubating said assay with detecting said transmissions of light on said assay to generate said test result.

2. The apparatus of claim 1, wherein said apparatus is adapted to perform a continuous image detection of said assay.

3. The apparatus of claim 1, further including an optics housing enclosing said optical detector and adapted to block debris from contact with said optical detector.

4. The apparatus of claim 1, further including a multichannel reader, whereby an assay reference coding activates a corresponding channel in said multichannel reader.

5. The apparatus of claim 1, wherein said reader monitors at least one pre-test parameter after said optical detector has acquired at least one image detection on said assay.

6. The apparatus of claim 5, wherein the image detection is an optical reflectance value.

7. The apparatus of claim 1, wherein said assay includes at least one test line and at least one control line, and whereby a theoretical reflectance value is a comparison between a reflectance value at said test line and a reflectance value at said control line.

8. The apparatus of claim 7, wherein an inadequate flow of sample along said assay triggers a detectable signal to deactivate said apparatus.

9. The apparatus of claim 7, wherein a reflectance value on said assay that is inconsistent with a theoretical reflectance value indicates a prior analyte test result development on said assay.

10. The apparatus of claim 1, wherein said incubator includes an insulated base.

11. The apparatus of claim 1, wherein said incubator is a temperature adjustable incubator comprising at least one temperature control.

12. The apparatus of claim 11, wherein said incubator compensates for localized temperature variations with an analog, proportional control circuit.

13. The apparatus of claim 1, wherein said light source comprises discrete light sources having light emitting diodes.

14. The apparatus of claim 13, wherein said light source includes a first mirror below said light source.

15. The apparatus of claim 14, wherein said light source includes a focusing lens adapted to receive light from said first mirror.

16. The apparatus of claim 1, further including a housing adapted to substantially enclose said reader and said incubator.

17. The apparatus of claim 1, further including a user interface having a display board.

18. An assembly to generate a test result from an assay, said assembly comprising:
   a. a reader having an optical detector detecting a first transmission of light on said assay and detecting at least a subsequent transmission of light on said assay;
   b. an incubator incubating said assay; and
   c. a housing substantially enclosing said incubator and said reader, said housing includes a cavity adapted to secure said assay and insulation adapted to withstand deformation during said incubation, and
   wherein said incubator incubates said assay concurrently as said reader generates said test result.

19. The assembly of claim 18, further including a user interface having an integrated circuit board supporting a display board.

20. The assembly of claim 18, wherein said assembly performs continuous image detection of said assay to generate said test result.

* * * * *

UNITED STATES PATENT AND TRADEMARK OFFICE
CERTIFICATE OF CORRECTION

PATENT NO. : 9,976,962 B2
APPLICATION NO. : 15/835979
DATED : May 22, 2018
INVENTOR(S) : Markovsky et al.

It is certified that error appears in the above-identified patent and that said Letters Patent is hereby corrected as shown below:

In the Specification

In Column 15, Line 13, --active-- should be "activate"

In Column 16, Line 10, --depends-- should be "depend"

In Column 17, Line 38, --position-- should be "positioned"

Signed and Sealed this
Seventeenth Day of July, 2018

Andrei Iancu
*Director of the United States Patent and Trademark Office*